United States Patent [19]
Schwanbom et al.

[11] 4,211,221
[45] Jul. 8, 1980

[54] RESPIRATOR

[75] Inventors: Erik Schwanbom; Hans-Joachim Hartwig, both of Lübeck; Detlef Warnow, Gross Grönau, all of Fed. Rep. of Germany

[73] Assignee: Drägerwerk Aktiengesellschaft, Fed. Rep. of Germany

[21] Appl. No.: 951,036

[22] Filed: Oct. 13, 1978

[30] Foreign Application Priority Data

Oct. 19, 1977 [DE] Fed. Rep. of Germany ....... 2746924

[51] Int. Cl.² ............................................. A61M 16/00
[52] U.S. Cl. ............................ 128/204.26; 128/204.18
[58] Field of Search ............... 128/145.5, 145.8, 145.6, 128/188

[56] References Cited

U.S. PATENT DOCUMENTS

| | | | |
|---|---|---|---|
| 3,951,143 | 4/1976 | Kitrilakis et al. | 128/145.8 |
| 3,976,064 | 8/1976 | Wood et al. | 128/145.6 |
| 4,003,377 | 1/1977 | Dahl | 128/145.8 |
| 4,057,059 | 11/1977 | Reid, Jr. | 128/145.8 |
| 4,098,272 | 7/1978 | Stewart | 128/145.6 |

Primary Examiner—Henry J. Recla
Attorney, Agent, or Firm—McGlew and Tuttle

[57] ABSTRACT

A synchronized intermittent mandatory ventilation respirator for providing inhalation and exhalation cycles to a patient while permitting the patient to carry out a complete inhalation and exhalation cycle spontaneously, comprising a gas supply adapted to be connected to a patient for supplying breathing gas under pressure to the patient, a main line connected to the gas supplied for supplying breathing gas to the patient, a main valve in the main line, and a timing system connected to the gas supply and the main valve for opening the main valve for a first selected timed inhalation cycle to supply breathing air to the patient and closing the valve for a selected timed exhalation cycle to permit the patient to exhale. A timer is connected to the main line downstream of the main valve, to the gas supply and to the timing system for blocking the connection between the timing system and the gas supply for stopping cycling of the timing system in response to a spontaneous inhalation of the patient and for supplying breathing air to the patient for a second selected timed inhalation cycle, and a trigger is connected to the main line downstream of the main valve and to the timing system for switching the timing system from an exhalation cycle to an inhalation cycle in response to a spontaneous inhalation of the patient.

10 Claims, 4 Drawing Figures

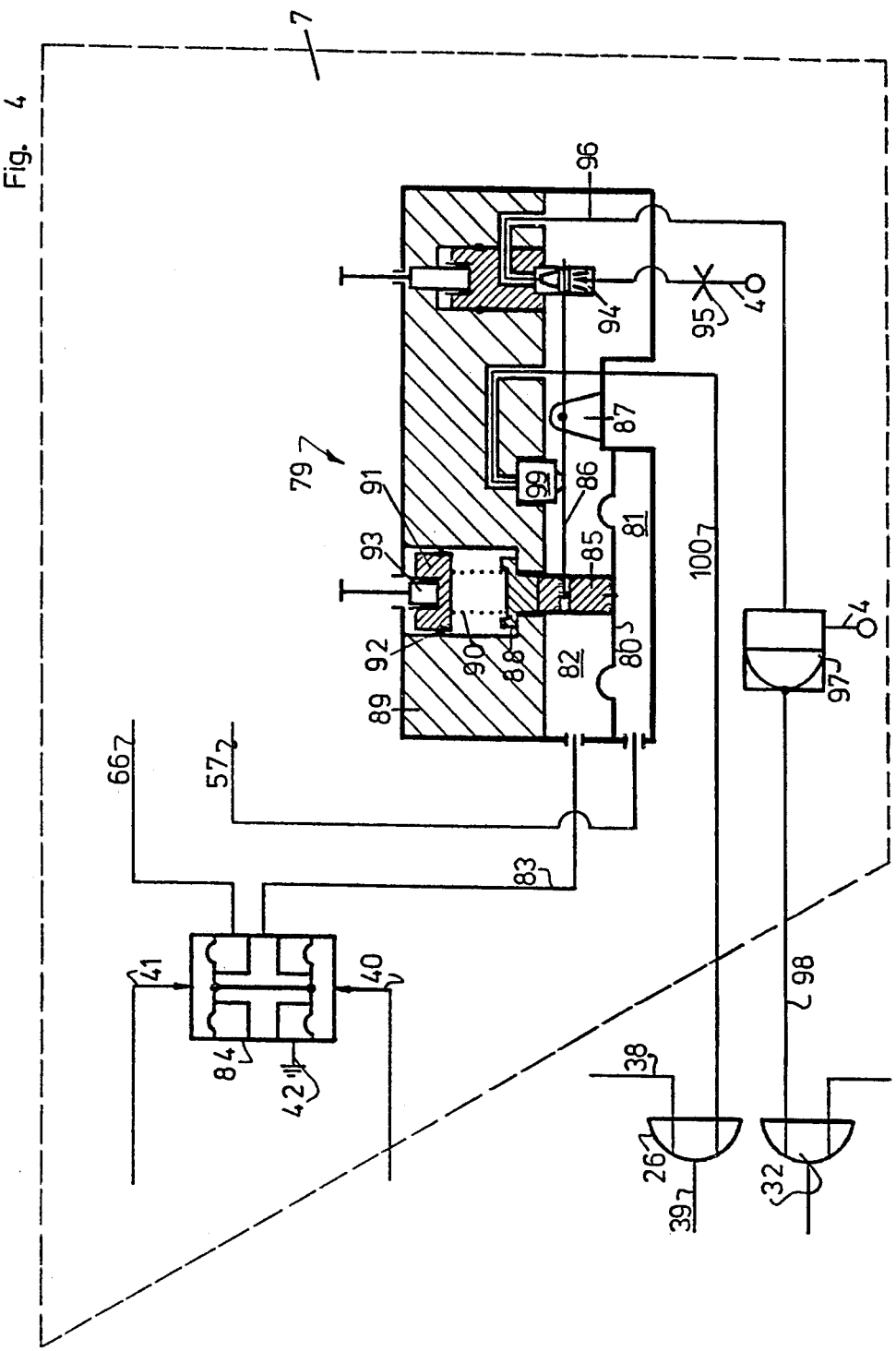

4,211,221

RESPIRATOR

FIELD AND BACKGROUND OF THE INVENTION

The present invention relates in general to respirators and in particular to a new and useful respirator which can be operated to provide synchronized intermittent mandatory ventilation to a patient.

DESCRIPTION OF THE PRIOR ART

A plurality of types of respirators are known, some of which are designed for special diseases, while a greater number permits a plurality of operating modes for adaptation to different physiological requirements.

For instance, vitally endangered premature births of newborn infants require, at first, intermittent positive pressure ventilation (IPPV), usually combined with positive exhalation end pressure (PEEP). After a recovery phase of the thoracic muscles and beginning normalization of the blood gas values in spontaneous breathing, respiratory gas having the necessary oxygen concentration can be given, possibly at continuously positive pressure (CPAP). After a long-term ventilation has been carried out, ventilation patients often suffer habituation, from which, without apparative assistance, they can return only to an insufficient spontaneous respiration. To break the habituation, ventilation is applied only after a certain number of spontaneous breathing cycles. The number of ventilation cycles imposed on the patient is then slowly decreased, until the patient is again able to breath by himself; that is IMV.

We must make sure that ventilation with the respirator, that is, any forced respiration, is begun only after the patient has completed the breathing cycle by exhalation, that is, that the patient's exhalation is not interrupted. This ventilation process is termed synchronized intermittent mandatory ventilation, abbreviated SIMV.

A pressure gas operated respirator is known with which the normal ventilation methods, including the IMV method, can be applied. Addition of the respiratory gas occurs by means of a piston valve, which is actuated by a fluid flipflop. The IMV method is controlled by means of a timer. The control pulse is received by the flipflop and is used for switching the piston valve whenever it happens to coincide with an inhalation phase of the patient. Inhalation, therefore, is then assisted by the additional admission of respiratory gas. But if the control pulse of the timer occurs during an exhalation phase of the patient, it switches back and starts a new cycle phase, the flipflop itself remaining inactive. The synchronization with the IMV process thus occurs only through the accidental coincidence of the control pulse with the inhalation phase. If this is not the case, the breath to be imposed, intended for dehabituation, is lost. The timer then starts with a new phase, that is, it begins anew (U.S. Pat. No. 3,976,065).

In another known respirator, the supply of air to the patient is also controlled by a flipflop circuit. By an exhalation timer and a patient trigger circuit the flipflop circuit is switched to its position for the inhalation half-cycle, and by an inhalation timer, a pressure limit trigger circuit and a volume limit sensor, to its position for the exhalation half-cycle. During the inhalation half-cycle a power valve for air supply to the patient is open and an exhalation valve closed, while during the exhalation half-cycle it is the other way around.

During ventilation by the SIMV process, the exhalation timer is preceded by a device whereby its switching time, i.e. the exhalation time, is made longer. In addition, a control circuit linked with the exhalation timer is activated. It switches the inhalation timer off, resets the exhalation timer, closes the exhalation valve during the controlled inhalation half-cycle and keeps it open during all other respirations, and switches on a delay means disposed between the output of the exhalation timer and the input of the flipflop circuit. SIMV proceeds as follows: Upon switching of the flipflop circuit to the exhalation half-cycle, the control circuit is actuated. It opens the exhalation valve and starts the time-delayed exhalation timer. During this phase the patient can exhale in spontaneous breathing, with the exhalation valve open, as well as inhale by means of the patient trigger circuit. After completion of the lengthened exhalation phase, the exhalation timer sends a signal to the delay device, in which it is delayed about 4 seconds. A trigger signal of the patient arriving during this delay of 4 seconds or, in the absence thereof, the signal from the delay device switches the flipflop circuit to the inhalation half-cycle.

At the same time the control circuit closes the exhalation valve and resets the exhalation timer. The patient is ventilated through the open power valve until a signal of the volume limit sensor, or of the pressure limit trigger circuit switches the flipflop circuit back to the exhalation half-cycle. Then the function sequence starts over again. The 4-second delay is to ensure synchronization of the forced ventilation with the exhausted lungs. For the trigger signal this is not necessary; during suction through the patient for inhalation the lungs are empty. The disadvantage of this known apparatus is the complicated circuit construction, which requires for the SIMV ventilation the switching in of a time extending device and a delay device for the 4 seconds (see German Patent DT-OS No. 26 37 366).

SUMMARY OF THE INVENTION

The invention provides a control of the ventilation with a respirator so that it can start only after complete exhalation, as the SIMV process demands. Yet the apparatus remains simple in its construction and easy to follow.

Accordingly, an object of the present invention is to provide a respirator for supplying breathing gas at selected timed inhalation and exhalation cycles for a patient while permitting the patient to carry out a complete spontaneous inhalation and exhalation on his own, comprising, gas supply means adapted to be connected to a patient for supplying a breathing gas under pressure, a main line connected to said gas supply means for supplying breathing gas to the patient, a main valve in said main line, timing means connected to said gas supply means and said main valve for opening said main valve for a first selected timed inhalation cycle to supply breathing air to the patient and closing said main valve for a selected timed exhalation cycle to permit the patient to exhale, a trigger connected to said main line downstream of said main valve and said timing means for switching said timing means from an exhalation cycle to an inhalation in response to a spontaneous inhalation of the patient, and a timer connected to said main line downstream of said main valve and said gas supply means and to said timing means for blocking the connection between said timing means and said gas supply means and stopping the cycling of said timing means in response to a spontaneous inhalation of the patient and for supplying breathing air to the patient for a second selected timed inhalation cycle.

A further object of the present invention is to provide a respirator which is simple in design, rugged in construction and economical to manufacture.

In the invention there is true synchronization. The ventilation, controlled by the pneumatic timing group for the inhalation phase of the timing system itself, starts with absolute certainty only after the fully completed exhalation phase, because actuation always occurs only by the timing system itself. During spontaneous breathing of the patient the timing system is turned off; it is turned on by the timer only after completion of the desired time for spontaneous breathing. A simple throttle in the timing group for the exhalation of the timing system makes sure that the exhalation phase is begun. The maximum time to start of ventilation is thus one exhalation phase. In case the patient should happen to be in an exhalation phase just then, he can set the timing system in motion via the trigger circuit by the inhalation following quite normally, and in so doing stop the normally starting exhalation phase and begin immediately with the inhalation phase. With the simply operating dependent controls, timing system-timer-trigger, a synchronous ventilation after the respective spontaneous breathing periods is ensured. The patient is ventilated immediately; inflation of the lungs when ventilation sets in before the lungs are fully exhaled is not possible.

The invention includes simple construction of the patient trigger circuit and of the timer for the spontaneous breathing. The solutions are obtained with pneumatic structural elements which are supplied from the ventilation gas reservoir.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

FIG. 4 is a schematic diagram, partly in section of the trigger.

DESCRIPTION OF THE PREFERRED EMBODIMENT

Figure 1:
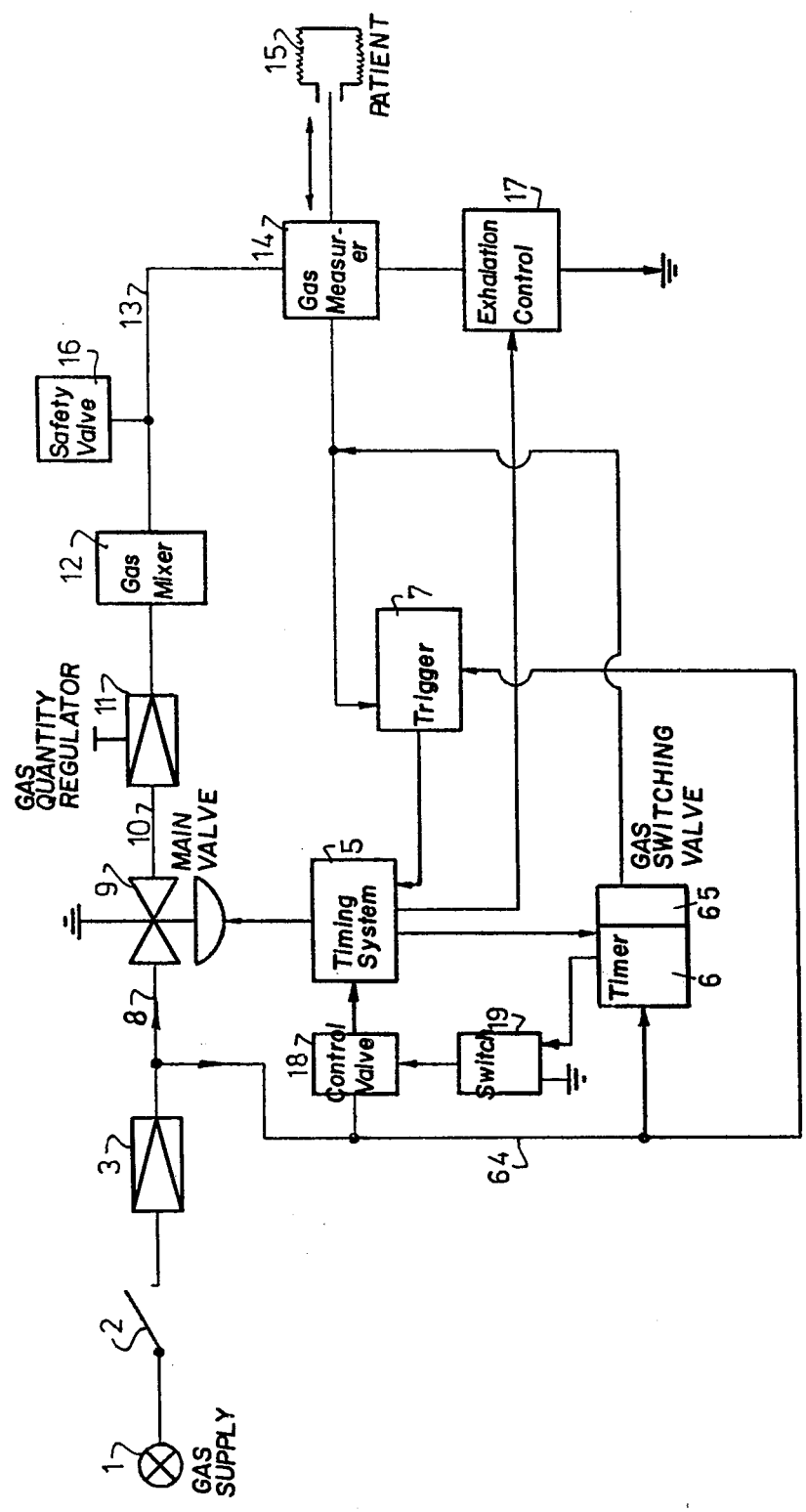
FIG. 1 shows a block diagram of the respirator with the timer constructed in accordance with the invention.

In the block diagram of FIG. 1, the functional groups of the respirator are represented linked together. Via the respiratory pressure gas connection or gas supply 1, ventilation gas is supplied to the main switch 2 and to the main pressure reducer 3, which establishes the operating pressure p in the apparatus. These elements comprise a gas supply means. Via line 64 all controls are supplied with gas under pressure. The controls are the automatic ventilation timing system 5 including a precontrol valve 18 and selecting switch 19, the spontaneous breathing timer 6 with respiratory gas switching valve 65, and the trigger 7. Via line 8 the ventilation gas flows to the main valve 9, which is actuated by the timing system 5 in the inhalation/exhalation rhythm.

The regulating element 11 in line 10 regulates the ventilation gas quantity, which flows to the internal gas mixing station 12 and then passes via line 13 to the respiratory gas measuring station 14 and thence to the symbolically represented patient 15. Connected to line 13 is the block "Safety" 16, which may contain a pressure limiting valve, an additional air valve or the like. Timing system 5 comprises inhalation/exhalation cycle timing means. Exhalation of the patient occurs via the respiratory gas measuring station 14 and the block "Exhalation Control" 17. Lines 8, 10 and 13 comprise a main line and 64 comprises a supplemental line.

In operation, when a patient at 15 is not breathing spontaneously, the patient is autmatically ventilated and permitted to exhale at timed cycles of inhalation and exhalation through the automatic ventilation timing system or means 5. If during an automatic exhalation period as produced by the timing system 5, the patient spontaneously inhales, trigger 7 will cause timing system 5 to switch into a ventilating or inhalation period thus supplying breathing air to the patient, in effect on the patient's demand. If the patient then continues normal breathing, automatic ventilation timing system 5 will be disconnected from the supplemental line 64 by the closing of control valve 18 and breathing will be controlled by the spontaneous breathing timer 6.

Figure 2:
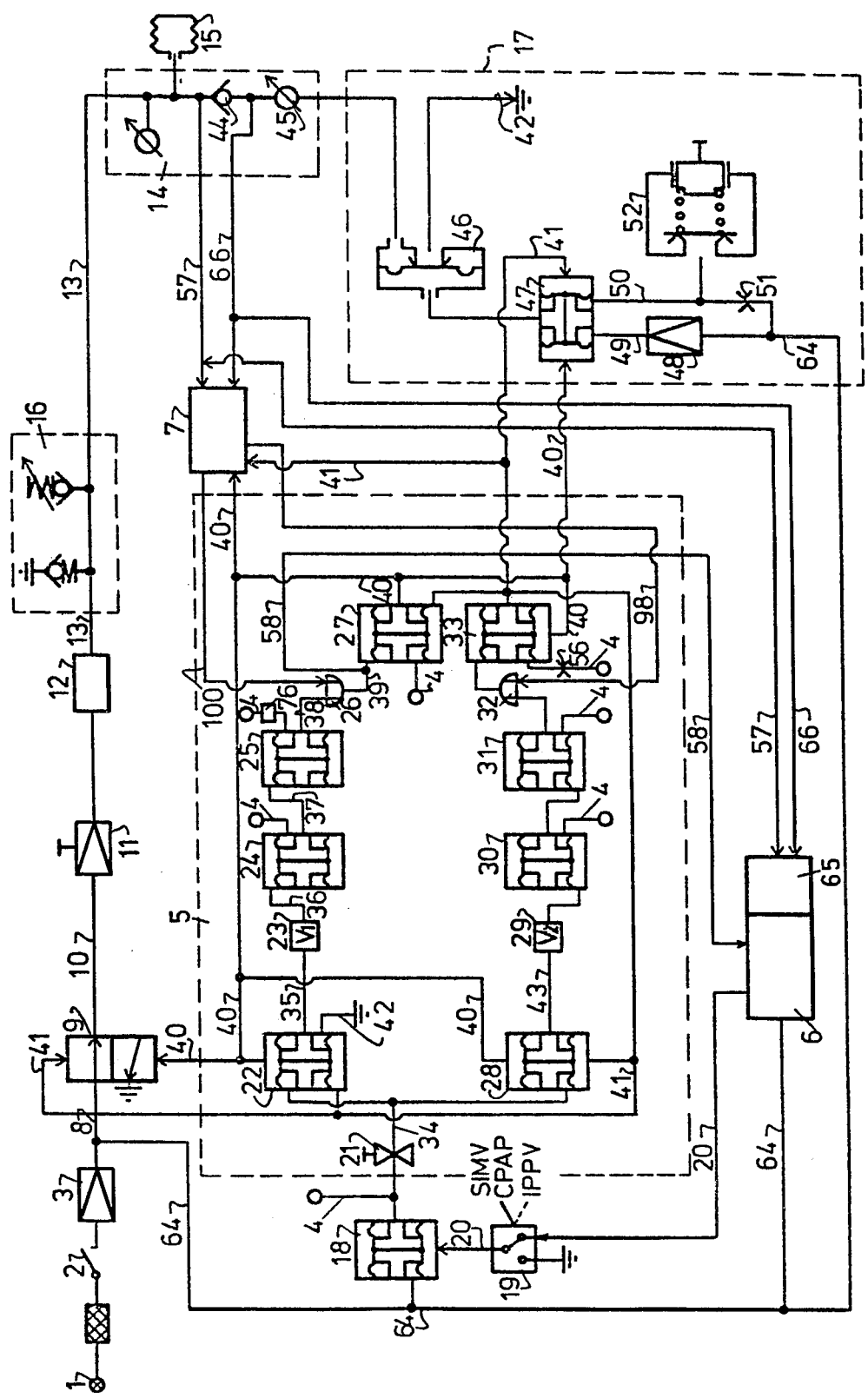
FIG. 2 is a circuit diagram of the SIMV process.

FIG. 2 shows the construction of the respirator with special consideration of the SIMV process. The main pressure reducer 3 reduces the supply pressure of the ventilation gas to the operating pressure p, with which the main valve 9 is supplied via line 8 and the timing system 5 via line 64. The precontrol valve 18 is located before or upstream of the timing system 5, which is controlled by the selecting switch 19. In the SIMV position, line 20 from timer 6 is connected with the precontrol valve 18; in the IPPV position it is separated.

The timing system 5 consisting of pneumatic structural elements 22 to 33 is connected with the precontrol valve 18 via line 34. It is pressure-supplied via line 34 and is regulated by the time regulating valve 21 in line 34. Regulation of the time periods for the inhalation and exhalation cycles occurs through two R-C or resistance-capacitance members with variable time constants, the R being formed with the time regulating valve 21 and the C or capacitance factor alternately from the volume $V_1$ at 23 and $V_2$ at 29, respectively. The R or resistance factor is variable by changing the setting of valve 21 which changes the resistance to the flow of gases in line 34. The alternate filling of the volumes $V_1$ 23 and $V_2$ 29 occurs through appropriate actuation of the first and second switching elements 22 and 23. The operation is as follows: In the absence of actuation of the precontrol valve 18 via line 20 (0 signal) pressure gas flows to the time regulating valve 21 via line 64. That is, when there is no pressure in line 20, as supplied from timer 6, and switch 19 is in it SIMV/CPAP position connecting timer 6 to valve 18, valve 18 is open so that lines 34 and 4 are pressurized by line 64. At the same time all switching elements of the timing system 5 are supplied with pressure gas via line 4. Terminals labelled 4 are assumed connected to each other. The metered pressure gas quantity (as regulated by valve 21) flows via line 34 to the switching element 22 and thence via line 35 to the volume $V_1$ 23. The pressure rise in volume $V_1$ 23 occurs simultaneously in third switching element 24 via line 36. The third switching element 24 at this moment is already pressurized with the gas pressure p via line 4 and thus maintains the fourth switching element 25 via line 37 in such a position that passage from line 4 (connected to element 25) to line 38 is blocked. As the pressure rise in first volume $V_1$ 23 reaches 80% of the operating pressure p (0.8 p), the switching element 24 reverses, so that passage from line 4 to line 37 is blocked and accordingly the passage from line 4 to line 38 in the switching element 25 is free. Since the pressure in the top chamber of element 25 supplied by line 37 drops below that in line 4. Through the first OR element 26 and line 39 there occurs the actuation of the first output element 27. Pressurization of the top chamber of output element 27 opens a passage between line 4 receives passage to exhalation control line 40. The output elements 27 and 33 are linked together so that they form a bistable storage unit. A 1-signal (1-signal-=operating pressure p) in line 40 of the first output element 27 actuates the second output element 33 so that line 41 has a 0-signal or low pressure therein. This 1-signal in line 40 is available at the same time at the switching element 22 and blocks passage from line 34 to line 35. Via line 35 the volume $V_1$ 23 is vented to the atmosphere 42. The 1-signal in line 40 pressurizes at the same time the second switching element 28, so that line 34 is connected with line 43 and thus second volume $V_2$ 29 is filled. Thus there proceeds in the structural elements 28 to 33 for the exhalation phase the identical process as in the structural elements 22 to 27 for the inhalation phase. Fifth switching element 30 and sixth element 31 act similarly to elements 24 and 25. If then the second output element 33 is controlled through so that a 1-signal is available in inhalation control line 41, the first output element 27 is thereby actuated so that line 40 has a 0-signal. The 0/1 signals in lines 40 and 41 control the rhythm or cycles of inhalation/exhalation by the setting of the time regulating valve 21.

While the overall time of one complete inhalation/exhalation cycle is variable by valve 21, the ratio between the inhalation part and the exhalation part of the total cycle is a fixed one which depends on the ratio between the volume $V_2$ and $V_1$.

The main valve 9 is switched by the 1-signal in line 41, whereupon the patient is supplied with ventilation gas. A 1-signal in line 40, however, closes the main valve 9, so that the patient receives no further ventilation gas and can start to exhale. Exhalation occurs via the check valve 44, the exhalation gas meter 45, and the exhalation valve 46 into the atmosphere 42. The exhalation valve 46 is actuated by the precontrol valve 47, which likewise is switched by the 0/1 signals in lines 40, 41. If during inhalation a 1-signal is available on line 41 and hence ventilation gas flows to the patient via the main valve, simultaneously the exhalation valve 46 is controlled shut through the 1-signal via the precontrol valve 47 and the back-pressure of the pressure reducer 48 via line 49. Reducer 48 is of course always supplied by pressure in line 64.

In the exhalation phase a 1-signal is available, on line 40, so that passage from line 49 to the exhalation valve 46 is blocked; instead, passage from line 50 to the exhalation valve 46 is free. Line 50 is supplied with pressure gas from line 64 via the throttle 51. The gas pressure in line 50 is regulated with the PEEP (positive endexpiratory pressure) valve 52 to set a desired exhalation resistance. Resistance between 0 and 30 mbar is possible by adjusting throttle 51.

Figure 3:
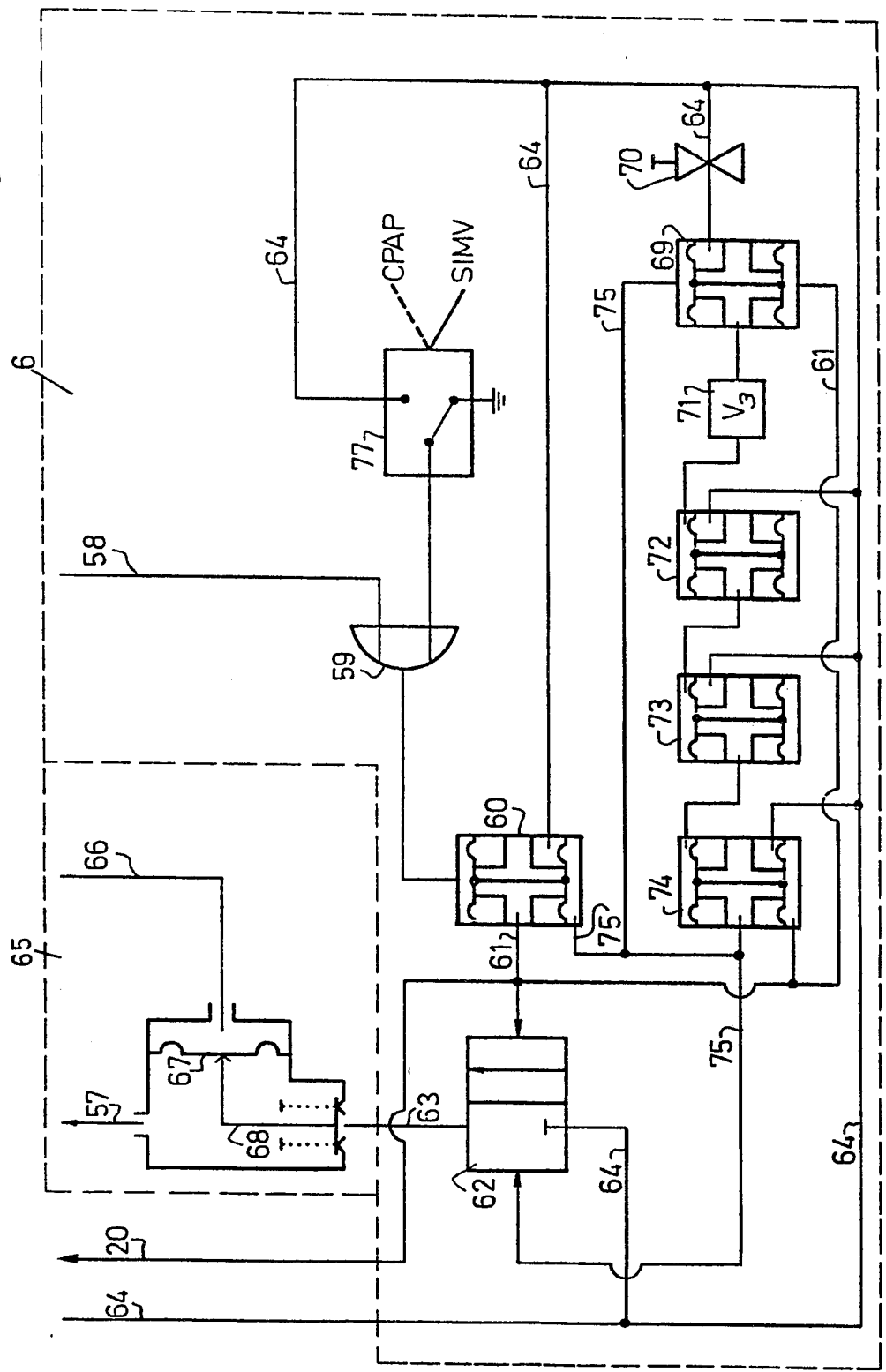
FIG. 3 is a circuit diagram of the timer and of the respiratory gas switching valve.

By timer 6 the patient's spontaneous breathing is controlled and at the same time a forced ventilation is brought about at adjustable intervals of time. During the spontaneous breathing phase, in which the patient himself breathes, there is available on line or control input 20 a 1-signal with which the precontrol valve 18 is actuated so that passage from line 64 to the time regulating valve 21 is blocked. Thereby ventilation via the timing system 5 and hence the forced ventilation is turned off. After this time span passes, the spontaneous breathing line 20 has a 0-signal, and thus passage from line 64 to line 4 and to the time regulating valve 21 is restored in the precontrol valve 18. Throttle 56 in line 4 to the second output element causes the through control in the first output element 27 to be completed faster, so that line 40 has a 1-signal sooner than line 41 and thus generates a 0-signal in line 41 through actuation of the second output element 33. It is thereby assured that the timing system 5 always begins with the exhalation phase. During the time span of the exhalation, either the patient can bring about, through trigger 7 via line 57, the triggering of a ventilation or inhalation phase immediately, or the timing system 5 itself assumes the ventilation after switching to the inhalation phase, after completion of the exhalation phase, that is at, an inhalation, the timing system 5 begins to switch to exhalation, with simultaneous formation of a 1-signal in line 39, which is then used via line 58 (FIG. 3) through the OR element 59 for the switching of the first switching element 60 in the timer 6, whereby spontaneous breathing is cleared again. Line 61 meanwhile has a 1-signal and controls the breathing gas valve 62 through so that passage from line 64 to line 63 exists. Via line 63 the lung machine respiratory gas switching valve 65 is supplied with ventilation gas. It delivers ventilation gas to the patient via suction or air lines 57 when a pressure difference exists between lines 57 and 66. This pressure difference occurs during suction—triggering—of the patient at the check valve 44, i.e. a lower pressure prevails in line 57 than in line 66. Membrane 67 moves the seal element with lever 68, so that ventilation gas can flow from line 63 into line 57. In addition, the 1-signal in line 61 actuates the second switching element 69 in the timer 6 so that the pressure gas metered in the time regulating valve 70 receives passage from line 64 to volume $V_3$ 71. With this the time span for spontaneous breathing begins. The sequence of the time control in the switching elements 72, 73 and 74 is identical with that in the switching elements 24, 25 and 27. If after pressure build-up of 0.8 p in volume $V_3$ 71 and corresponding through control of the switching elements a 1-signal is available in line 75, it controls the switching valve 62 shut, so that passage from line 64 to line 63 is interrupted and thus the time spane for spontaneous breathing is ended. Simultaneously the passage from the time regulating valve 70 to volume $V_3$ 71 is blocked. Volume $V_3$ 71 vents backward. Likewise the 1-signal blocks the switching element 60 in line 75. Line 61 thus has a 0-signal, as does also line 20. Thereby the timing system 5 is released or reactivated again.

To prevent a 1-signal from occurring in line 39 and line 58 immediately via fourth switching element 25, line 4, line 38, to the first OR element 26, a time delay 76 is installed in the line 4 to the switching element 25. This prevents timer 6 from switching the timing system 5 off again immediately via line 20 after the switching element 25 receives a 0-signal from line 38.

By switch 77 timer 6 possesses a possibility of switching from the SIMV process to the CPAP process.

In the CPAP position, OR element 59 is always supplied with a 1-signal through line 64 to keep valve 62 open and supplying gas to line 57.

The essential components of the trigger 7 shown in FIG. 4 are the pressure switch 79 and the venting valve 84. The pressure switch 79 has as a switching element a membrane 80 between sealed first and second pressure chambers 81 and 82. The pressure chamber 81 is connected with the patient 15 via suction and air line 57, pressure chamber 82 with the venting valve 84 via line 83. The venting valve 84 receives during the inhalation phase a 1-signal via the connected line 41. It is thereby controlled so that in this breathing phase line 83 is vented to the atmosphere 42.

During the exhalation phase the venting valve 84 receives a 1-signal via the connected line 40. With it line 83 is connected with differential pressure line 66. The pressure difference occurring at the check valve 44 during triggering can thus be transmitted via line 57 and the connection of lines 66, 83 to the pressure chambers 81 and 82.

The movement of membrane 80 during a pressure difference in the pressure chambers 81 and 82 is transmitted through the guide 85 to the lever 86. Lever 86 is rotatably mounted in the bearing 87. On guide 85 is loosely placed the spring guide 88, which on the side of the movement direction toward the membrane 80 is fixed in the housing 89 by a stop and toward the opposite side is supported by means of spring 90. Spring 90 is limited by the piston 91 which is axially displaceable and sealed from the housing 89 by means of the seal ring 92. The displacement of piston 91 occurs by a rotary movement of the threaded setting member 93.

During triggering (suction) by the patient, the pressure difference forming at membrane 80 causes a movement of membrane 80 in the direction of the pressure chamber 81. Guide 85 coupled with membrane 80 transmits the movement to lever 86, which is moved counterclockwise. In so doing the other lever arm of lever 86 gets into the switching zone of the jet nozzle 94. There occurs an interruption of the gas jet which leads from line 4 via throttle 95, via the jet nozzle 94 into line 96. This interruption is reflected in a pressure variation which in the pneumatic amplifier 97 is converted to a 1-signal in patient inhalation indication line 98 which leads to the second OR element 32. Through the actuation of second output element 33 there is thus generated in line 41 a 1-signal with which a ventilation of the patient is triggered. A resulting pressure rise in line 13 and hence also in lines 57 and 66, but not in line 83, leads to pressure increase in the pressure chamber 81. With a force thereby resulting on membrane 80, which is greater than the counter-force from spring 90, guide 85 moves so that lever 86 is caused to move clockwise. With this movement the micro-switch 99 is switched, which then generates a 1-signal in line 100 connected to the first OR element 26. With the controlling through of the first OR element 26 via line 39 to the first output element 27 there results in line 40 a 1-signal. With this signal the exhalation phase is initiated.

It is evident from the above description that after the ventilation initiated with the trigger the exhalation phase is initiated already after one breath, namely after reaching a desired ventilation pressure adjustable at the setting member 93. Without trigger the exhalation phase is terminated after completion of the inhalation phase set in the time regulating valve 21.

While a specific embodiment of the invention has been shown and described in detail to illustrate the application of the principles of the invention, it will be understood that the invention may be embodied otherwise without departing from such principles.

What is claimed is:

1. A synchronized intermittent mandatory ventilation respirator for providing selected timed inhalation and exhalation cycles to a patient while permitting the patient to carry out a complete spontaneous inhalation and exhalation on its own comprising, gas supply means adapted to be connected to a patient for supplying a breathing gas under pressure, a main line connected to said gas supply means for supplying breathing gas to the patient, a main valve in said main line, a supplemental line connected to said main line upstream of said main valve, automatic ventilation timing means connected to said supplemental line and said main valve for opening said main valve for a first selected timed inhalation cycle to supply breathing gas to the patient and closing said main valve for a selected timed exhalation cycle to permit the patient to exhale, gas measuring means connected to said main line for sensing a patient induced pressure change in said main line formed by a spontaneous inhalation and a spontaneous exhalation of the patient, trigger means connected to said supplemental line, to said gas measuring means and to said timing means for switching said timing means from an exhalation cycle to an inhalation cycle in response to a spontaneous inhalation of the patient, and spontaneous breathing timer means connected to said supplemental line, to said gas measuring means and to said automatic ventilation timing means for blocking the connection between said automatic ventilation timing line and said supplemental means and stopping the cycling of said automatic ventilation timing means in response to a spontaneous inhalation and exhalation of the patient and for supplying breathing air to the patient from said supplemental line for a second selected timed inhalation cycle, and permitting the exhalation of the patient.

2. A respirator according to claim 1 further including a pre-control valve connected between said supplemental and said timing means, having a control input connected to said timer, said timer producing a control signal in said control input in response to a spontaneous inhalation of the patient for closing said pre-control valve and blocking the flow of breathing gas from said gas supply means to said timing means.

3. A respirator according to claim 2 further including a selector switch connected between said pre-control valve and said timer at said control input for removing the connection between said timer and said pre-control valve.

4. A respirator according to claim 1 wherein said timing means comprises a first and second switching element each having an input connected to said supplemental line and an output, an exhalation control line connected to each of said first and second switching element for closing said first switching element and opening said second switching element, and inhalation control lines connected to each of said first and second switching elements for opening said first switching element and closing said switching element, said outputs of said first and second switching elements connected respectively to first and second volumes having respective sizes corresponding to said selected timed inhalation cycle and exhalation cycle respectively and each having an output, third, fourth, fifth and sixth switching elements each having an input connected to said supplemental line and each having an output, said first volume connected to said third switching element for closing said element after said selected timed inhalation cycle, said output of said third switching element connected to said fourth switching element for closing said fourth switching element when said third switching element is open, said second volume connected to said fifth switching element for closing said fifth switching element after said selected timed exhalation cycle, said output of said fifth switching element connected to said sixth switching element for closing said sixth switching element, first and second OR elements connected to respective outputs of said fourth and sixth switching elements and each including an output, a first output element connected to said output of said first OR element including an input connected to said supplemental line and an output connected to said exhalation control line, a second element connected to said output of said second OR element having an input connected to said supplemental line and an output connected to said inhalation control line, said inhalation and exhalation control lines each connected to said main valve for respectively opening and closing said main valve, and said inhalation and exhalation control lines connected to said trigger, said trigger including a patient inhalation indication line connected to an input of said second OR element for opening said second output element in said timing means and initiating said first selected timed inhalation cycle.

5. A respirator according to claim 4, further including a time regulating valve connected between said supplemental line and said first and second switching elements, said time regulating valve being adjustable to effect selection of said first selected timed inhalation cycle and said selected timed exhalation cycle, said first and second volumes being adjustable to select the ratio between said first selected timed inhalation cycle and said selected timed exhalation cycle.

6. A respirator according to claim 1, further including a check valve in said gas measuring means downstream of the connection in said main line to the patient, a suction line connected between said main line upstream of said check valve and said trigger, a differential pressure line connected between said main line downstream of said check valve and said trigger, said timing means including first and second OR elements each having an output, said outputs of said first and second OR elements connected respectively to first and second output elements for respectively initiating said timed exhalation cycle and said first timed inhalation cycle, and first and second control lines connected to said trigger and each connected respectively to an input of said first and second OR elements for initiating an inhalation cycle in said timing means when a patient spontaneously inhales, thereby causing a differential in pressure between said suction line and said differential pressure line.

7. A respirator according to claim 6, wherein said trigger further includes a pressure switch having first and second pressure chambers, a switching membrane separating said first and second pressure chambers, said suction line connected to said first pressure chamber, said differential pressure line connected to said second pressure chamber, a lever pivotally mounted in said pressure switch having one arm connected to said switching membrane and an opposite arm, a jet nozzle connected between said gas supply means and one output of said trigger connected to said second OR element, a microswitch engaged with said lever and connected to said other output line connected to said first OR element, whereby a spontaneous inhalation by the patient causes deactivation of said microswitch and interruption of flow in said jet nozzle for switching said timing means from a selected timed exhalation cycle to an inhalation cycle.

8. A respirator according to claim 7 further including a venting valve having an input connected to said differential pressure line and an output connected to said second pressure chamber, said venting valve connected to said inhalation and exhalation control lines for opening said venting valve during an exhalation cycle and closing said venting valve during an inhalation cycle, said venting valve further connected to the atmosphere for communicating said second pressure chamber with the atmosphere during an inhalation cycle.

9. A respirator according to claim 1 further including a check valve in said gas measuring means downstream of the connection between said main line and the patient, said timer including a respiratory gas switching valve, a suction line connected between said respiratory gas switching valve and said main line upstream of said check valve, a differential pressure line connected between said respiratory gas switching valve and said main line downstream of said check valve, a breathing gas switching valve connected between said respiratory gas switching valve and said gas supply means, a first switching element having an input connected to said gas supply means and an output connected to said breathing gas switching valve for opening and closing said breathing gas switching valve, a second switching element connected to said output of said first switching element and having an input connected to said gas supply means and an output connected to a volume corresponding with said second selected timed inhalation cycle, at least one additional switching element having an input connected to said gas supply means and an output connected to said first switching element and said breathing gas switching valve and connected to said volume for switching said breathing gas switching valve off after said second selected timed inhalation cycle.

10. A respirator according to claim 9 wherein said timer further includes a switch connected to said gas supply means, an OR element having an input connected to said switch, said switch switchable from one position connecting said gas supply means to said OR input and another position connecting said OR input to the atmosphere, said OR element having a second input connected to said timing means and an output connected to said first switching element.

* * * * *